United States Patent [19]

Bhatia

[11] Patent Number: 5,023,350
[45] Date of Patent: * Jun. 11, 1991

[54] PROCESS FOR THE PURIFICATION OF CYCLIC ESTERS

[75] Inventor: Kamlesh K. Bhatia, Newark, Del.

[73] Assignee: E. I. Du Pont de Nemours and Company, Wilmington, Del.

[*] Notice: The portion of the term of this patent subsequent to May 30, 2006 has been disclaimed.

[21] Appl. No.: 528,632

[22] Filed: May 24, 1990

[51] Int. Cl.$^5$ ............................................ C07D 319/00
[52] U.S. Cl. .................................................. 549/274
[58] Field of Search .................................. 549/274, 518

[56] References Cited

U.S. PATENT DOCUMENTS 4,835,293  5/1989  Bhatia .................................. 549/274

Primary Examiner—C. Warren Ivy
Assistant Examiner—Ba K. Trinh
Attorney, Agent, or Firm—Charles E. Krukiel

[57] ABSTRACT

This invention relates to a gas-assisted vaporization process for purifying cyclic esters such as glycolide, lactides and mixtures thereof which enables the cyclic ester to be rapidly separated from its impurities as a vapor component of a gas stream. The process includes a solvent-scrubbing step for recovering the cyclic ester from the gas stream.

12 Claims, No Drawings

PROCESS FOR THE PURIFICATION OF CYCLIC ESTERS

FIELD OF THE INVENTION

This invention relates to a process for purifying glycolide, lactides and mixtures thereof. More specifically, it relates to a gas-assisted vaporization process whereby the cyclic ester can be rapidly separated as a gas stream from its less volatile impurities. More particularly, it relates to such a process which includes a solvent scrubbing step for recovering the cyclic ester from the gas stream and thereby effecting the separation of any volatilized impurities. Still more particularly, the invention relates to a process as above for preparing polymer grade glycolide and L-lactide.

PRIOR ART

Cyclic esters are polymerizable intermediates to the corresponding polyesters of alpha-hydroxycarboxylic acids. Polymers of glycolide and the various isomeric lactides are of particular interest for biomedical uses, for example, as surgical sutures and staples. Such uses require that the cyclic esters be very pure so that they can be polymerized to the high molecular weight polymers required for extrusion to high tension strength filaments (or other forms depending upon the medical application). For example, the suture grade glycolide is generally required to be of sufficient purity to provide a polymer of inherent viscosity (I.V., an indirect measure of the polymer molecular weight) of at least 1.1, but no more than 1.6 for ease of extrusion, as measured in a hexafluoroisopropyl alcohol solution at 0.1 deciliter per gram concentration at 30° C., as referenced in U.S. Pat. No. 4,650,851.

Cyclic esters, such as glycolide and lactides, are typically prepared by polymerizing the corresponding alpha-hydroxycarboxylic acid to an oligomer, i.e., relatively low molecular weight polymer, which is then thermally cracked to a crude cyclic ester distillate. It is well known that the crude product prepared in this way contains large amounts of acid and other impurities which can be separated by solvent washing, charcoal treatment and multiple recrystallizations using suitable solvents. For example, to purify crude glycolide, Lowe, U.S. Pat. No. 2,668,162 (1954), employs charcoal treatment and two to three recrystallizations using chemically pure ethyl acetate; Bellis, U.S. Pat. No. 4,727,163, employs two recrystallizations using ethyl acetate to obtain 99+% pure glycolide. The product purified by such means can be polymerized to produce polymer for extrusion into films and fibers but is not sufficiently pure to produce the high molecular weight, high tensile polymers required, for example, for sutures.

To obtain highly pure cyclic esters, several methods are disclosed in the art but they are not entirely satisfactory. Schmitt et al., U.S. Pat. No. 3,597,450 (1971), teaches that suture grade glycolide could be obtained by subjecting the impure glycolide to the dual sequential steps of recrystallization and sublimation. The sublimation step at 75° to 130° C. requires highly reduced pressures less than 2.5 mm Hg and as low as 0.07 mm Hg, is very slow, takes 12 to 17½ hours, and is therefore not very practical for large scale operation. Rhum et al., U.S. Pat. No. 4,650,851 (1987), describes a process for further purifying commercially available glycolide that has already been purified by several recrystallizations. The process involves treating the glycolide as a solution in a suitable organic solvent, such as $CH_2Cl_2$, with alumina under controlled conditions for 1 to 60 minutes, filtering to remove the alumina, and recovering the purified glycolide from the solution by evaporating the solvent. Dieter and Schwall, German Patent Application 3 636 188 (1988), purify glycolide to polymer grade material by continuously distilling it in a forced-discharge reactor under reduced pressure (e.g., 0.1-5 mbar) and an increasing temperature gradient (e.g., 15°-200° C.).

It should also be noted that recently issued Bhatia, U.S. Pat. No. 4,835,293, discloses a gas-assisted process for the depolymerization of poly(alpha-hydroxycarboxylic acids), such as polyglycolic and polylactic acids, to the corresponding cyclic ester, i.e., glycolide and lactides, in a high state of purity. The disclosed process constitutes a significant advance in the depolymerization art. For example, it directly produces glycolide as high as 99.9% pure, but does not always directly produce glycolide of sufficiently purity for direct conversion to suture grade polyglycolic acid ester. For suture grade the glycolide should generally be more than 99.9% pure, preferably it should be purer than 99.93%.

As pointed above, the prior art purification processes are not entirely satisfactory. They suffer one or more drawbacks, such as entailing high product losses and/or requiring a multiplicity of costly steps, including multiple recrystallizations, distillation or sublimation under highly reduced pressures at rather long residence times.

It is the object of this invention to provide a novel process for purifying impure glycolide and lactides that overcomes substantially all of the disadvantages of the prior art.

It is another object to provide a gas-assisted vaporization process for purifying cyclic esters that enables the cyclic esters to be rapidly separated from their impurities as a vapor component of a gas stream and to be recovered from the gas stream in a high state of purity and in high yield (recovery).

It is a further object to provide such vaporization process that can be operated at atmospheric pressure. Still another object is to recover the cyclic ester from the gas stream by solvent-scrubbing. A particular object is to provide a process as above for purifying impure glycolide and lactides into polymer grade material without requiring a reduced pressure distillation or lengthy sublimation step.

SUMMARY OF THE INVENTION

A process for purifying an impure cyclic ester selected from the class consisting of glycolide, lactides and mixtures thereof, which process comprises (i) feeding the impure cyclic ester to a stripping device, (ii) maintaining the cyclic ester molten in the stripping device at a temperature and pressure below its boiling point, (iii) intimately contacting the molten cyclic ester with a flow of a substance that is gaseous at said temperature and pressure and inert to the cyclic ester, (iv) removing the gas stream containing cyclic ester from the stripping device, and (v) recovering cyclic ester from the gas stream having a higher purity than the impure cyclic ester.

This invention is based on the discovery that the separation of a cyclic ester such as glycolide or a lactide from impurities therein can be effected efficiently, rapidly and substantially completely by means of a gas-assisted process as defined, particularly where there is created a high interfacial area between the molten cyclic ester and the gas, and the flow rate of the gas and its amount relative to that of the cyclic ester are sufficiently large so that vapors of the cyclic ester can be carried rapidly and substantially completely from relatively non-volatile impurities in the molten material.

The stripping step should be carried out under conditions such that the cyclic ester being purified does not get converted to its polymer in significant amounts. In general, the stripping rate is higher at higher temperatures, but higher temperatures also increase the rate of polymerization. Addition of depolymerization catalysts, e.g., antimony trioxide, were found to convert the molten cyclic ester to its polymer even more rapidly. The polymerization is believed to be catalyzed by acid impurities, but addition of substances, such as calcium oxide, to neutralize the acids were also found to increase the polymerization rate.

Therefore, the stripping should be conducted without the addition of such substances and the acid impurities in the feed cycle ester should be low. It should be conducted at a rapid rate so that the cyclic ester is not held at the stripping temperature for long periods. However, it should be noted that any portion of the cyclic ester that gets converted to its polymer does not represent a yield loss, because the polymer can be depolymerized back to its cyclic ester at a higher depolymerization temperature in the presence of depolymerization catalysts.

Various embodiments of the invention include: feeding the cyclic ester intermittently to minimize its holdup at the stripping temperature; conducting the purification step continuously and stripping the cyclic ester while keeping it molten in a thermally stable, high boiling liquid medium.

It will be appreciated by those skilled in the art that use of a gaseous stripping agent for the cyclic ester does not require that the temperature of the cyclic ester to be purified be raised to its normal boiling point. Nor does it require that the pressure be reduced to promote vaporization of the cyclic ester. The temperature need only be such that the cyclic ester exerts sufficient vapor pressure for practical operation. Thus, the purification process can be operated at ordinary pressures and at temperatures that are low relative to the boiling point of the cyclic ester. Consequently, yield-lowering side reactions, e.g., degradations, racemization and thermally-induced ring-opening polymerization of the cyclic ester, especially in the presence of the impurities, which may catalyze the polymerization, can be minimized.

The invention process offers numerous other advantages over the art. It can substantially reduce the time required to separate the cyclic ester from its impurities. It is also capable of substantially completely separating the cyclic ester from its impurities. The subject vaporization technique is superior to distillation, including under highly reduced pressure. Also, being able to operate at atmospheric or near atmospheric pressure can reduce investment and operating costs by eliminating the need for costly equipment employed in sublimation and distillation at reduced pressures. In fact, the purification process of this invention can be carried out in the same equipment as that used for preparing the cyclic ester initially by the atmospheric process. Bhatia, U.S. Pat. No. 4,835,293. Furthermore, by using the same solvent for product recovery during purification as well as during initial cyclic ester preparation, yield loss is minimized because the filtrate from the purification step can be used in the subsequent cyclic ester preparation. Also the stripping gas at atmospheric and higher pressures provides an inert atmosphere and eliminates product degradation from potential air leaks at reduced pressures. Further, glycolide and lactides are obtainable in polymer grade purities directly without a reduced pressure or sublimation post treatment.

The term lactide as used herein is meant to include L-lactide, D-lactide, racemic D,L-lactide and meso-lactide, used singly or as mixtures of one or more thereof. L-lactide is the preferred lactide.

By polymer grade glycolide is meant glycolide that yields a polymer that has at least an inherent viscosity of 1.1 as measured in a hexafluoroisopropyl alcohol solution as referenced above.

By a polymer grade lactide is meant such material that is also acceptable to the industry for producing medical grade polymers.

DETAILED DESCRIPTION OF THE INVENTION

In general, the process is conducted by feeding a cyclic ester as defined into a stripping device maintained at a temperature at which the ester is molten and exerts a significant vapor pressure but is below its normal boiling point, and intimately contacting it with a stream of a gaseous stripping agent, hereinafter gas, to produce a gas stream saturated with vaporized cyclic ester. The resulting gas stream containing cyclic ester vapors is removed from the stripping device, leaving behind less volatile impurities.

The thus-purified cyclic ester may be recovered from the gas stream by any means known in the art. For example, it may be recovered directly by condensation to solid glycolide or lactide. Alternatively, the cyclic ester can be recovered from the gas stream by solvent-scrubbing. One such solvent-scrubbing method and the solvents useful therein are disclosed in Bhatia, U.S. Pat. No. 4,835,293, which disclosure is incorporated herein by reference. Preferred scrubbing solvents are polar liquids that have high solvency for such polar materials as water and hydroxycarboxylic acids and low solvency for glycolide and lactides. Representative of such solvents is isopropyl alcohol. Other solvents such as ethyl acetate or acetone may also be used. The solubility of glycolide, for example, in isopropyl alcohol is about 1% by weight at ambient temperatures. Thus, scrubbing the gas stream with isopropyl alcohol effectively removes any water or carboxylic acid carried along with the cyclic ester from the gas stream, and results in a more highly pure cyclic ester product. Glycolide and L-lactide, for example, are normally solid, crystalline materials at ambient temperatures and are readily separated from a scrubbing liquid by ordinary means such as filtration. The filtrate containing dissolved product can be recycled as scrubbing solvent for subsequent cyclic ester preparation.

Solvents such as ethyl acetate and acetone which have higher solvency for cyclic esters may also be used and pure cyclic ester recovered by recrystallization.

If desired, the gas-stripping of vapors of the cyclic ester may be conducted in the presence of a higher-boiling thermally stable and inert solvent or diluent for the cyclic ester, such as a high molecular weight poly(tetraalkyleneether glycol) or a high-boiling heat-transfer medium, to further help minimize the possibility of localized overheating and polymerization of the cyclic ester during the stripping step. The cyclic ester may be fed to the stripping zone batchwise, intermittently or continuously. The gaseous material, however, will normally be fed to the stripping device substantially continuously, including rapidly intermittent and pulsed feeding, so as to maximize the rate at which vaporized cyclic ester can be stripped from the molten mass.

The gaseous agent for stripping/carrying the cyclic ester out of the stripping device may be any substance that is gaseous and stable at the operating temperatures and pressures and is inert to the cyclic ester. It may be normally gaseous, such as nitrogen, argon, carbon dioxide, carbon monoxide or low molecular weight hydrocarbon. It may be normally non-gaseous but gaseous at reaction temperature and pressure. Preferred is $N_2$ for its inertness and ready availability. Preferably, the gas will be preheated to or reasonably close to the operating temperature and will be injected below the surface of the molten material in the stripping zone; for example, introduced below the agitator of a stirred tank reactor or fed into the bottom of a vertically disposed reactor so that it can counter-currently contact down-flowing the cyclic ester.

The flow rate of the gas should be sufficiently high so as not to limit the cyclic ester production rate. If the flow rate is too low, the yield of cyclic ester may be adversely affected since the gas functions importantly to carry the cyclic ester as vapor out of the reactor. This technique allows one to run a short residence time continuous process and thereby minimize product losses resulting from degradation and polymerization reactions.

The flow rate of the gas, relative to the cyclic ester, will depend upon the particular cyclic ester and the stripping temperature. One skilled in the art can determine the gas flow rate from the vapor pressure of the cyclic ester at the stripping temperature to achieve a desired stripping rate. It should be further understood that the stripping should be sufficiently rapid so that the cyclic ester is not held at the stripping temperature for any long period that would cause polymerization.

The temperature for stripping cyclic ester away from its non-volatile and relative non-volatile impurities can vary widely, but normally will be in the range of from about 140° to about 215° C. depending upon the cyclic ester being treated. For example, the optimum temperature for glycolide is preferably from about 150° to 190° C. In general, the higher the temperature, the faster the rate of recovery of the purified cyclic ester but the rate of formation of polymerized by-product also increases.

The pressure may vary from sub-atmospheric to atmospheric and super-atmospheric. Preferably it is atmospheric with a small back pressure imposed on the gas stream by downstream equipment, which should be designed to keep the back pressure as low as practical, for example, less than 5 psi.

The stripping device may be of any design know in the art for effecting intimate gas-liquid contact. It may be a stirred tank with gas sparging means, preferably one which admits the gas directly under the agitator. Also, the reactor may be a sieve-plate column, or one adapted to spray the molten material into the stripping zone as droplets, or one adapted to dispose the molten cyclic ester as a falling film or multiplicity of films.

One suitable reactor design for stripping cyclic ester from its impurities in accordance with the method of the invention comprises a vertically-disposed sieve-plate column equipped with means for feeding liquefied cyclic ester at or near the top of the column, means for removing residual liquid material from the bottom of the column, means for feeding the gaseous stripping agent at or near the bottom of the column such that it can pass up through the down-coming cyclic ester composition in the column, an exit means at the top of the column for removing the gas stream containing cyclic ester, and heating means for maintaining the column contents at the desired operating temperature.

The cyclic ester to be fed to the stripping device in a continuous feed embodiment, such as that described above, is generally preheated and fed molten to the stripping device. Alternatively, it may be fed as a solution or as a slurry in a suitable, i.e., inert and non-interfering, solvent such as acetone. Preferably the cyclic ester is preheated to the operating temperature to reduce the heat load on the column. In a batch or an intermittent process the cyclic ester can be fed as a solid and heated to the stripping temperature in the stripping device.

The examples that follow are intended to illustrate the invention and are not to be construed as limiting it to any particular embodiment described herein. The equipment employed was a stirred tank reactor in conjunction with a solvent-scrubbing system employing reagent grade isopropyl alcohol as the scrubbing solvent, all essentially as described in Bhatia, U.S. Pat. No. 4,835,293.

EXAMPLE 1

Approximately 500 gms of Terethane ® 2000 poly(tetramethyleneether glycol) was placed in a stirred vessel used as the reactor in the above referenced patent and preheated to 124° C., i.e., above the melting point of glycolide. 50 gms of dry solid glycolide [prepared by the method of Bhatia, U.S. Pat. No. 4,835,293 and having a purity of 99.7 to 99.8% as determined by differential scanning calorimetry (DSC) but not suitable for making suture grade polyglycolic acid] was charged to the vessel under agitation. The glycolide melted in a few minutes, and then a stream of dry nitrogen ($N_2$) was passed through the mixture at a rate of 0.1 standard cubic foot per minute (scfm) while the temperature of the vessel was increased to 148° C. When the glycolide appeared in the recovery train the $N_2$ flow rate was increased to 0.35–0.4 scfm. The stripped glycolide was recovered from the $N_2$ stream by scrubbing with isopropanol. During this time the run was interrupted twice to remove a glycolide pluggage of the transfer line which had caused leakage at the joints at the head of the stripping vessel. After 1 hour from the feeding of the initial glycolide charge, a second 50 gm charge of the glycolide was added to the reaction zone and the run was continued for another 25 minutes at 155 to 157° C. and a $N_2$ flow rate of 0.46 scfm. 35.4 gms of refined glycolide was recovered from the isopropyl alcohol-glycolide slurry in the scrubber by filtration and drying under reduced pressure.

The product was found to contain no detectable acid impurities by titration. The product was 99.97 mole percent pure by DSC with a melting point of 85.3° C. Furthermore, no detectable impurities were found by IR and NMR analyses. The analyses for heavy metals were below detectable amounts and thus totalled less than 5 parts per million. A sample of this product was polymerized under standard conditions and the resulting polymer had an inherent viscosity of 1.14.

By stripping a portion of the isopropyl alcohol filtrate under reduced pressure it was found that the filtrate contained 4.9 gms of glycolide. This does not represent a loss since this filtrate could be employed for subsequent cyclic ester preparation.

EXAMPLE 2

This Example illustrates the purification of 99.65% pure glycolide, as determined by DSC, made on a large scale. The product contained some acetone insoluble material and polymerized to polyglycolic acid having an inherent viscosity of only 0.56, as determined under standard conditions. 25 gms of this glycolide was charged to a small stripping vessel similar to that described in Example 1 but without the stirrer. It was melted and stripped at 144°-150° C. with $N_2$ at a flow rate of 0.24 scfm over about 1 hour. 12.4 gms of refined polymer grade glycolide was recovered from the alcohol scrubbing medium. As in Example 1, the product was found to be highly pure. It was 99.95% pure by DSC, contained no acetone insolubles, and was, thus, suitable for polymerizing to the high molecular weight suture grade polymers.

The glycolide remaining in the flask was allowed to cool down and was stripped again the next day at 172°-183° C. for about 30 minutes, i.e., till only 1 gm remained in the flask. Five additional gms of refined glycolide from the isopropyl alcohol scrubbing medium were obtained. Additionally about 3.8 gms of glycolide were found on the walls of the apparatus. The isopropyl alcohol filtrate weighed 87 gms and was evaporated under reduced pressure and found to contain another 1.1 gms of glycolide.

I claim:

1. A process for purifying an impure cyclic ester selected from the group consisting of glycolide, lactides and mixtures thereof, which process comprises
   (i) feeding the impure cyclic ester to a stripping device,
   (ii) maintaining the cyclic ester molten in the stripping device at a temperature and pressure below its boiling point,
   (iii) intimately contacting the molten cyclic ester with a flow of a substance that is gaseous at said temperature and pressure and inert to the cyclic ester,
   (iv) removing the gas stream from the stripping device, and
   (v) recovering the cyclic ester from the gas stream having a higher purity than the impure cyclic ester.

2. The process of claim 1 wherein the pressure is at least about atmospheric pressure.

3. The process of claim 2 wherein the cyclic ester and the gaseous substance are fed substantially continuously to the stripping device and the gas stream is removed substantially continuously therefrom.

4. The process of claim 1 wherein the cyclic ester is stripped at a temperature in the range of from about 140° to 215° C.

5. The process of claim 4 wherein the cyclic ester is glycolide and the temperature is in the range of from 150° to 190° C.

6. The process of claim 1 wherein the cyclic ester is recovered from the gas stream by solvent scrubbing.

7. The process of claim 6 wherein the scrubbing solvent is a polar solvent in which the impurities are more soluble than the cyclic ester.

8. The process of claim 7 wherein the cyclic ester is substantially insoluble in the solvent.

9. The process of claim 8 wherein the solvent is isopropyl alcohol.

10. The process of claim 6 wherein the cyclic ester is glycolide.

11. The process of claim 6 wherein the cyclic ester is a lactide.

12. The process of claim 6 wherein the lactide is L-lactide.

* * * * *